United States Patent [19]

Williams

[11] Patent Number: 4,859,233
[45] Date of Patent: Aug. 22, 1989

[54] 2,3,6-TRICHLOROBENZOHYDROXAMIC ACID DERIVATIVES

[75] Inventor: John W. Williams, Lake Bluff, Ill.

[73] Assignee: Sandoz Ltd., Basel, Switzerland

[21] Appl. No.: 147,409

[22] Filed: Jan. 25, 1988

Related U.S. Application Data

[63] Continuation-in-part of Ser. No. 95,787, Sep. 11, 1987, abandoned, which is a continuation of Ser. No. 907,348, Sep. 12, 1986, abandoned.

[30] Foreign Application Priority Data

Jul. 24, 1987 [EP] European Pat. Off. ........ 87810412.4

[51] Int. Cl.$^4$ ..................... A01N 37/44; C07C 153/11
[52] U.S. Cl. ........................................ 71/100; 71/111;
71/115; 558/254; 560/34; 560/39; 562/439;
562/444
[58] Field of Search ................. 558/254, 256; 71/100,
71/111, 115; 560/34, 39; 562/439, 444

[56] References Cited

U.S. PATENT DOCUMENTS 3,702,863 11/1972 Neighbors ............................. 71/114

FOREIGN PATENT DOCUMENTS 0133155 2/1985 European Pat. Off. ............. 71/114

Primary Examiner—Bruce Gray
Attorney, Agent, or Firm—Gerald D. Sharkin; Richard E. Vila

[57] ABSTRACT

Disclosed are herbicidal compounds of the general formula I;

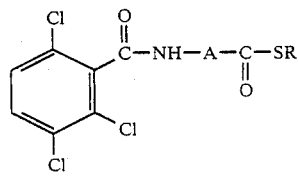

wherein A is O-alkylene of 1 to 5 carbon atoms, O-alkenylene of 3 to 6 carbon atoms in which the unsaturation is non-adjacent the oxygen atom thereof or NH-alkylene in which the alkylene is of 1 to 5 carbon atoms, and —COZR is an acid function or forms certain ester or thioester functions, and the mono- and di-salt forms thereof.

21 Claims, No Drawings

2,3,6-TRICHLOROBENZOHYDROXAMIC ACID DERIVATIVES

This application is a continuation-in-part of application Ser. No. 095,787, filed Sept. 11, 1987 which in turn is a continuation of application Ser. No. 907,348, filed Sept. 12, 1986, now both abandoned.

The present invention relates to compounds which are derivatives of 2,3,6-trichlorobenzoic acids, particularly benzohydroxamic acid derivatives, their use as herbicides and to agricultural compositions containing the same. The present invention more particularly relates to compounds of the formula I:

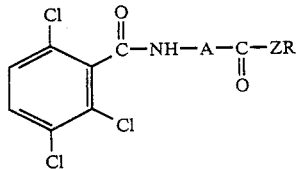

wherein
A is O-alkylene of 1 to 5 carbon atoms, O-alkenylene of 3 to 6 carbon atoms in which the unsaturation is non-adjacent the oxygen atom thereof or NH-alkylene in which the alkylene is of 1 to 5 carbon atoms, the O— and NH— thereof being attached to the NH which is adjacent to A,
Z is oxygen or sulfur,
R is H, $C_1$-$C_{12}$alkyl, $C_3$-$C_8$alkenyl, $C_3$-$C_8$alkynyl, $C_2$-$C_{10}$haloalkyl containing 1 to 6 halogens of atomic weight of 18 to 80, $C_2$-$C_{10}$alkoxyalkyl, cycloalkyl or cycloalkenyl of 3 to 8 ring carbon atoms optionally substituted by 1 or 2 halogens of atom weight of 18 to 80 or $C_1$-$C_2$alkyl groups, cloalkylalkyl or cycloalkenylalkyl of 4 to 10 carbon atoms in which the alkyl portion is of 1 to 3 carbon atoms and the cycloalkyl or cycloalkenyl ring is of 3 to 8 carbon atoms and is optionally mono- or di-ring substituted by halo of atom weight of 18 to 80 or $C_1$-$C_2$alkyl groups or

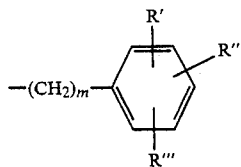

m is 0 to 3,
R' and R" are independently H, $C_1$-$C_4$alkyl, $C_1$-$C_4$alkoxy, $C_1$-$C_4$alkylthio, $CF_3$, halo of atomic weight of from 18 to 80 or $NO_2$,
R''' is H, $C_1$-$C_3$alkyl or halo of atomic weight of 18 to 80, or
two of R', R" and R''' together form $C_1$-$C_2$alkylenedioxy with the other being H,
and the salt forms thereof.

When in the compounds of the formula I, A is O-alkylene or NH-alkylene, the alkylene may be straight chain or branched. Any such branching, e.g. methyl groups, may occur once or twice on any carbon atom of the linear portion of the alkylene moiety. Preferably, the alkylene portion of the O-alkylene moiety is of 1 to 3 carbons and contains no more than a single methyl branch, or is unbranched. More preferably, A is —OCHR$_1$—, wherein R$_1$ is H or methyl, and it is particularly preferred that A is O-methylene, i.e. —OCH$_2$—.

When A is O-alkenylene, the alkenylene portion may also be straight chain or branched. Preferably, the connecting linear alkenylene portion is of 3 or 4 carbon atoms and contains no more than a single methyl branch or is unbranched, and is more preferably unbranched, e.g. allylene.

In general, Z is preferably oxygen.

When R is or contains an alkyl, alkenyl, alkynyl or alkoxy group, the same may be straight chain or branched, provided that any alkenyl or alkynyl group desirably comprises at least a three linear carbon atom chain. When R is alkyl, it is preferably $C_1$-$C_8$alkyl, branched or unbranched, more preferably $C_1$-$C_6$alkyl. When R is haloalkyl, it preferably contains one or two halogen atoms or one or two $CF_3$ groups. When R is or contains a cycloalkyl or cycloalkenyl group, such group is preferably unsubstituted. When R is cycloalkylalkyl or cycloalkenylalkyl, the alkyl portion may be straight chain or branched, but is more preferably unbranched and of 1 or 2 carbon atoms, and it particularly preferred that such alkyl is methyl (—CH$_2$—). When R is or contains phenyl, it is generally preferred that m is 0 or 1. Preferably, the phenyl portion or group is unsubstituted, mono-substituted or disubstituted. In particular, it is generally preferred that R' is H, $C_1$-$C_4$alkyl, $C_1$-$C_2$alkoxy, $CF_3$, halo of atomic weight of from 18 to 80 or nitro, R" is H and R''' is H, $C_1$-$C_2$alkyl or halo of atomic weight of from 18 to 80. More preferably, R' is H, $C_1$-$C_3$alkyl, methoxy, $CF_3$, F, Cl or nitro, R" is H and R''' is H, $CH_3$, F or Cl.

The alkali metal and ammonium salts are the generally preferred salt forms. When R is H and disalt forms may be produced, the mono-salt forms are generally preferred.

The compounds of the formula I in which A is O-alkylene in free base form may be prepared in a Procedure A by reacting the compound of the formula II:

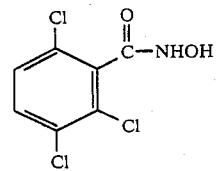

with a compound of the formula III:

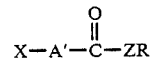

wherein R is as above defined, A' is alkylene of 1 to 5 carbon atoms and X is halo, preferably chloro or bromo.

Procedure A may be carried out at temperatures of from about 25° C. to 150° C., preferably 60° C. to 120° C. in the presence of a base and in a solvent media. Preferred bases are the alkali metal hydroxides such as sodium hydroxide or potassium hydroxide. Preferred solvents are the lower alkanols such as methanol or ethanol or a mixture of water and a lower alkanol, e.g. water and ethanol. The desired product of the formula I may be isolated and recovered by working up by established procedures.

The compounds of the formula I in which R is H may also be obtained in a procedure B by hydrolysis of a compound I in which R is other than H. Such hydrolysis may be carried out in a conventional manner by treating an ester of the formula I in water and a water miscible organic solvent such as tetrahydrofuran at temperatures of from 0° C. to 100° C., more suitably 10° C. to 80° C., in the presence of a base, followed by treatment of the resulting salt form, preferably in an aqueous media, with an acid to effect acidification. The resulting product of the formula I in which R is H may be isolated and recovered by working up by established procedures.

The compounds of the formula I in which A is NH-alkylene in free base form may be prepared in a Procedure B by reacting the compound of the formula IV:

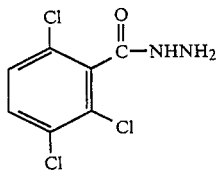     IV with a compound of the formula V:

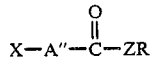     V wherein Z and R are as above defined, X is halo, preferably chloro or bromo, and A" is alkylene of 1 to 5 carbon atoms.

Procedure B may be carried out at temperatures of from about 20° C. to 120° C., preferably 40° C. to 90° C., in the presence of a base and in a solvent media. A typically preferred base for such reaction is sodium carbonate. Preferred solvents include the acyclic and cyclic ethers such as tetrahydrofuran. The desired product may be isolated and recovered from the Procedure B reaction mixture by working up by standard procedures.

The compounds of the formula I in which R is other than H may be produced from other compounds of the formula I in which R is other than H by the well-known process of transesterification (Procedure C). In such procedure a compound of the formula I is subjected to reaction with the alcohol or thioalcohol corresponding to the ester desired to be formed, i.e. a compound HZR (Compound VI) in the presence of transesterification catalyst and in a liquid media of conventional type. Transesterification catalysts are well known and include the Lewis acids such as the metal alkoxides, e.g. titanium n-butoxide. Such procedure is generally carried out in a known manner to shift the equilibrium of reaction system in favor of the desired ester of the formula I such as by causing removal in predetermined form from the reaction solvent media of the —ZR moiety of the starting material desired to be replaced, e.g. by forming the corresponding alcohol HOR which is selectively evaporated from the reaction media. The reaction may be carried out at varying temperatures typically of from about 25° C. to 150° C., more typically about 50° C. to 120° C., and in a convention solvents which are typically chosen as appropriate in accordance with the predetermined plan for the reaction. The preferred starting compounds of the formula I are those in which —ZR is O-$C_1$-$C_2$alkyl, more preferably the methyl ester, and the equilibrium shifted in favor of the desired ester of the formula I by evaporating the resulting $C_1$-$C_2$alkanol. For example, the methanol from the preferred methyl ester starting material may be evaporated from an inert aromatic solvent such as toluene. The resulting desired ester of the formula I may be isolated and recovered from the Procedure C reaction by working up by established procedures.

The compounds of the formula I have the tautomeric form:

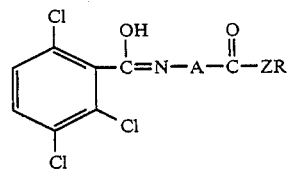

wherein A, Z and R are as defined. Such enols of the compounds I are of acid character and form, and accordingly the compounds I will also form salts even when R is other than H. Since the compounds in which R is H form salts, the compounds of the formula I in which R is H form di-salts. When R is H, salt formation preferentially takes at the ZH site, such that the mono-salt forms of those in which such R is H are those in which such R is the salt-forming cation at such location.

The mono- and di-salts forms of the compounds of the formula I may be prepared in a conventional manner by reacting a compound of the formula I with a salt forming base in a solvent media. Temperatures may vary widely but are usually in the range of 0° C. to 100° C., more typically 10° C. to 60° C. Solvents typically employed for such salt formation include the ethers and mixtures thereof with water. When the mono-salt form of the compounds I in which R is H is desired, the formation of such mono-salt in good yield by avoiding substantial quantities of the di-salt form may be effected by various established techniques such as control of the amount of salt-forming base employed or by taking advantage of the differential solubility of the desired mono-salt form in the reaction solution. Also, the mono-salt forms may be prepared by using an excess of the salt-forming reagent to thereby form to di-salt and subjecting the di-salt to moderate heating under high vacuum to form the mono-salt from the di-salt form. Heating at temperatures of from 60° C. to 120° C. for 12 to 36 hours is usually adequate to form the mono-salts from the di-salts. In general, the salt forms of the compounds I may be isolated and recovered by employing standard procedures.

The compounds of the formula I generally form salts with bases and all such salt forms are included within the invention. In addition to exhibiting herbicidally activity of similar character to the parent non-salt forms, the various salt forms may also be employed to prepare other salt forms by employing well-known procedures. While the preparation of the salt forms has been separately described above, such preparation may take place in conjunction with or prior to recovery in other type procedures hereinabove described for preparation of the compounds of the formula I, in which case the desired salt may be recovered or converted to the salt free form by employing standard procedures.

The preferred salt forms of the compounds of the formula I are the alkali metal salts, particularly the sodium and potassium salts, and the ammonium salt forms including the secondary and tertiary ammonium salt forms. Merely representative of some of the wide variety of secondary and tertiary ammonium salt forms are the dimethylammonium salt, isopropylammonium salt, diethanolammonium salt, triethanolammonium salt and the 2-hydroxyethyloxyethylammonium salt. Other salt forms which may be prepared include the hydrazinium salt forms which may be derived from unsubstituted or substituted hydrazine, e.g. hydrazine, $NH_2N(CH_2CH_3)_2$ and the like.

The compound of the formula II employed in Procedure A may be prepared from 2,3,6-trichlorobenzoic acid chloride as described in Step B of Example 1 hereinafter. The compound of the formula IV employed in Procedure B may be also prepared from 2,3,6-trichlorobenzoic acid chloride as described in Example 4 hereinafter. The preparation of 2,3,6-trichlorobenzoic acid chloride is indicated in Step A of Example 1 hereinafter. The various other starting materials used in preparation of the compounds of the formula I and its salts are either known or may be prepared from known materials by conventional methods.

The compounds of the formula I (including the salts thereof) are useful because they control the growth of plants. By plants it is meant germinating seeds, emerging seedlings and established vegetation including underground portions. In particular, the compounds are useful as herbicides as indicated by cassing damage to both monocotyledoneous and dicotyledoneous plants in various standard evaluations for determining such effects, particularly to dicotyledoneous plants. The herbicidal effects are exhibited both pre- and post-emergence the plants. Such herbicidal effects indicate that the compounds of the formula I are particularly of interest in combatting weeds (unwanted plants) in a locus in which such weeds are present.

The present invention therefore also provides a method of combatting weeds in a locus which comprises applying to the locus a herbicidally effective amount of a compound of the invention. When employed in crops as selective herbicides, the compounds of the invention will be applied in any amount sufficient to combat weeds in the crop locus without substantially damaging the crop.

For general herbicidal as well as selective herbicidal use of the compounds of the invention, the particular amounts to be applied will vary depending upon recognized factors such as the compound employed, the plants primarily in the locus, the timing, mode and formulation in application, the various conditions of treatment such as soil and weather and the like. However, in general, satisfactory results in weed control are usually obtained upon application of the compounds of the invention at a rate in the range of from 0.1 to 10 Kg./hectare, more usually 0.3 to 5 Kg./hectare, and preferably 0.5 to 3 Kg./hectare, the application being repeated as necessary.

For practical use as herbicides, the compounds of the formula I may be and are preferably employed in herbicidal compositions comprising a herbicidal effective amount of the compound and an inert carrier which is agriculturally acceptable in the sense of not, by reason of its presence, poisoning the agricultural environment including the immediate soil of application or any crops present therein or otherwise being unsafe for application. Such compositions or formulations may contain 0.01% to 99% by weight of active ingredient, from 0 to 20% by weight of agriculturally acceptable surfactants and 1 to 9.9% by weight of the inert carrier. Higher ratios of surfactant to active ingredient are sometimes desirable and are achieved by incorporation into the formulation or by tank mixing. Application forms of composition typically contain between 0.01 and 25% by weight of active ingredient, but lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful compositions or formulations of the compounds of the invention include dusts, granules, pellets, suspension concentrates, wettable powders, emulsifiable concentrates and the like. They are obtained in a conventional manner, e.g. by mixing the compounds of the invention with the inert carrier. More specifically, liquid compositions are obtained by mixing the ingredients, fine solid compositions by blending and, usually grinding, suspensions by wet milling and granules and pellets by impregnating or coating (preformed) granular carriers with the active ingredient or by agglomeration techniques.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wattable powders, which can be dispersed in water or oil to any desired concentration of the active compound, can be prepared by incorporating wetting agents into concentrated dust compositions.

Alternatively, the compounds of the invention may be used in microencapsulated form.

Agriculturally acceptable additives may be employed in the herbicidal compositions to improve the performance of the active ingredient and to reduce foaming, caking and corrosion.

Surfactant as used herein means agriculturally acceptable material which imparts emulsifibility, spreading, wetting, dispersibility or other surface-modifying properties. Examples of surfactants are sodium lignin sulphonate and lauryl sulphate.

Carriers as used herein mean a liquid or solid material used to dilute a concentrated material to a usable or desirable strength. For dusts or granules it can be e.g. talc, kaolin or diatomaceous earth, for liquid concentrate forms, a hydrocarbon such as xylene or an alcohol such as isopropanol; and for liquid application forms, e.g. water or diesel oil.

The compositions of this invention can also comprise other compounds having biological activity, e.g. compounds having similar or complementary herbicidal activity or compounds having antidotal, fungicidal or insecticidal activity.

A typical herbicidal composition, according to this invention, is illustrated by the following Examples A and B in which the quantities are in parts by weight.

EXAMPLE A

Preparation of a Dust

| Preparation of a Dust | |
|---|---|
| Product of example 1 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

EXAMPLE B

Preparation of Wettable Powder

25 Parts of a compound of formula I, e.g. the compound of Example 1 hereinafter, are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE 1

Methyl(2,3,6-trichlgrobenzoyl)aminooxy]acetate

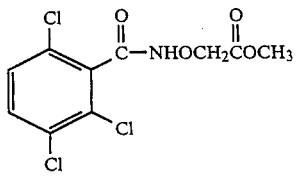

Step A: 2,3,6-trichlorobenzoyl chloride

To 70 g. thionyl chloride was added 90 g. of 2,3,6-trichlorobenzoic acid. This was stirred and heated to reflux (ca. 20° C.) for 2.5 hours. The reaction mixture was allowed to cool and excess thionyl chloride evaporated in vacuo. More (25 ml.) of thionyl chloride was added and the mixture heated at reflux for an additional 2 hours. The thionyl chloride was evaporated under reduced pressure to give 2,3,6-trichloro2-methoxybenzoyl chloride as a yellow oil.

Step B: 2,3,6-trichlorobenzohydroxamic acid

To a solution of 81 g. of potassium carbonate in 110 ml. of water and 400 ml. of diethyl ether cooled to 5° C. was added 40.5 g. of hydroxylamine hydrochloride and 110 g. of 2,3,6-dichloro-benzoyl chloride. After addition was complete, the reaction mixture was stirred and allowed to warm to ambient temperature over a 1 hour period. The mixture was then acidified with 20% HCL, and the organic layer separated. The aqueous layer was extracted with 200 ml. of ethyl acetate, and the combined organic layers dried over magnesium sulfate and concentrated in vacuo to give a light brown viscous oil which was purified by high pressure liquid chromatography to yield an oil of 2,3,6-trichlorobenzohydroxamic acid.

Step C: [(2,3,6-trichloro-benzoyl)aminooxy]acetic a

To a solution of 4.9 g. of potassium hydroxide in 50 ml of water and 350 ml. of tetrahydrofuran and 23.2 g. of 2,3,6-trichloro-benzohydroxamic acid was added 11.6 g of methyl bromoacetate. The mixture was stirred at room temperature for 60 hours, the solvents evaporated in vacuo, the residue dissolved in ethyl acetate and washed twice with 5% HCl, 590 sodium bicarbonate, again with 590 HCL, then 50% NaCl and dried over MgSO4. The solvent was evaporated in vacuo and the residue chromatographed using high pressure liquid chromatography. The fraction containing the product was crystallized from ethanol/hexane to yield methyl[2,3,6-trichlorobenzoyl)aminooxy]acetate, m.p. 102°–105° C.

EXAMPLE 2

[(2,3,6-Trichlorobenzoyl)aminooxy]acetic acid

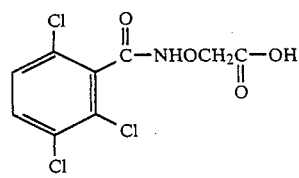

To 1.25 g. of potassium carbonate in 15 ml. of water and 35 ml. of tetrahydrofuran was added 2.0 g. of methyl [(2,3,6-trichlorobenzoyl)aminooxy]acetate and the resulting mixture was stirred at 50° C., for 2 days. The solvents were evaporated in vacuo and residue dissolved in dilute aqueous sodium hydroxide, washed with ethyl acetate and the aqueous layer acidified with concentrated hydrochloric acid. The resulting aqueous layer was extracted with two portions of ethylacetate, the combined ethyl acetate layers were dried over MoSO4 and concentrated in vacuo to obtain [2,3,6-trichlorobenzoyl)aminooxy]acetic acid, m.p. 145°–147° C.

EXAMPLE 3 n-Butyl[(2,3,6-trichlorobenzoyl)aminooxy)]acetate

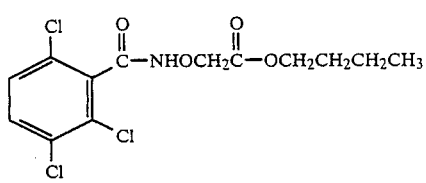

A mixture of 1.8 g. of methyl[2,3,6-trichlorobenzoyl)aminooxy]acetate, 50 ml of n-butanol and approximately 20 mg. of O-p-tolnenesulfonic acid was warmed to 100° C. overnight. Excess alcohol was evaporated in vacuo and the residue taken up in chloroform, washed with aqueous 5% sodium bicarbonate, dried over MgSO4, filtered, and evaporated in vacuo to give titled compound as a liquid.

Additional representative compounds of the invention are exemplified below with reference to the structural formula I.

| Ex. No. | A | R | m.p.(°C.) |
|---|---|---|---|
| 4 | —OCH2— | O—isopropyl | — |
| 5 | " | O—ethyl | wax |
| 6 | " | O—n-propyl | liquid |
| 7 | " | O—t-butyl | — |
| 8 | " | O—hexyl | — |
| 9 | " | O—cyclopentyl | — |
| 10 | " | O—p-chlorophenyl | — |

| Ex. No. | A | R | m.p.(°C.) |
|---|---|---|---|
| 11 | " | O—benzyl | — |
| 12 | " | O—cyclopropylmethyl | — |
| 13 | " | O—CH₂(2,4-dichlorophenyl) | — |

EXAMPLE 4

2,3,6-trichlorobenzoylhydrazine

To a solution of 0.22 mol. hydrazine in 100 ml. chloroform at −10° C. was added 0.1 mol of 2,3,6-trichlorobenzoyl chloride. The mixture was stirred at ambient temperature for 2 hours, filtered, and the filtrate evaporated in vacuo. The residue was crystallized from methanol and water, then recrystallized from chloroform and hexane to obtain the titled product.

The herbicidal toxicity of the compounds of this invention can be illustrated by established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds.

Twenty-four hours or less after the seeding, the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of from 14 to 21 days, at which time the condition of the plants and the degree of injury to the plants was rated on a scale of from 0 to 10, as follows: 0=no injury, 1, 2=slight injury, 3, 4=moderate injury, 5, 6=moderately severe injury, 7, 8, 9=severe injury, 10=death and NE indicated not emerged.

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the various weed species that have attained a prescribed size. After spraying, the plants were placed in a greenhouse and watered daily or more frequently. Water was not applied to the foliage of the treated plants. The severity of the injury was determined 21 days after treatment and was rated on the scale of from 0 to 10 heretobefore described.

Table I below indicated results obtained in an evaluation of the compound of Example 1 above, in the above-described greenhouse tests at an application rate of 0.5 pounds per acre.

TABLE I

| Plant | Pre-emergence Rating | Post-emergence Rating |
|---|---|---|
| Velvetleaf | 9 | 9 |
| Pigweed | NE | 9 |
| Crabgrass | NE | 6 |
| Barnyard grass | 9 | 6 |
| Yellow foxtail | 9 | 5 |
| Soybeans | 9 | 10 |

The below indicated compounds of formula I were screened in similar tests employing a plant set comprising *Abutilon theophrasti, Amaranthus retroflexus, Sinapis alba, Solanum nigrum, Bromus tectorum, Setaria viridis, Avena fatua* and *Echinochloa crus-galli* and application rates corresponding with 1 and 4 kg/ha. The results which are given in Table 7, below, indicate a herbicidal activity of the compounds of formula I which is superior over similar prior art compounds. In the following Table 7 the standard is the compound of Example 1.2 of the EPA No. 133 155.

TABLE 7

| Test Compound appl. time | Example 3 | | Example 5 | | Standard | |
|---|---|---|---|---|---|---|
| | pre-em | post-em | pre-em | post-em | pre-em | post-em |
| appl rate kg/ha | 1 4 | 1 4 | 1 4 | 1 4 | 1 4 | 1 4 |
| Abutilon | 8 10 | 8 10 | 10 10 | 8 9 | 8 8 | 4 6 |
| Amaranthus | 10 10 | 9 9 | 10 10 | 9 10 | 5 7 | 4 6 |
| Sinapis | 9 9 | 7 9 | 9 10 | 8 8 | 4 7 | 4 5 |
| Solanum | 10 10 | 9 9 | 9 10 | 9 10 | 3 8 | 7 8 |
| Bromus | 5 7 | 4 5 | 4 8 | 4 6 | 1 9 | 5 6 |
| Setaria | 7 8 | 6 8 | 8 8 | 5 7 | 1 6 | 1 3 |
| Avena | 8 8 | 3 3 | 8 8 | 4 5 | 1 4 | 1 7 |
| Echinochlor | 8 8 | 5 7 | 8 9 | 5 5 | 1 5 | 1 3 |

The compounds of the formula I in other specific property evaluations were also indicated to have the desired properties of good soil persistence and less soil mobility compared with the very good commercial herbicide Dicamba.

What is claimed is:

1. A compound of the formula:

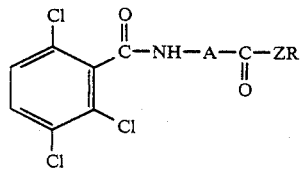

wherein

A is O-alkylene of 1 to 5 carbon atoms, O-alkenylene of 3 to 6 carbon atoms in which the unsaturation is non-adjacent the oxygen atom thereof or NH-alkylene in which the alkylene is of 1 to 5 carbon atoms, the O— and NH— thereof being attached to the NH which is adjacent to A, Z is oxygen or sulfur, R is H, $C_1$-$C_{12}$alkyl, $C_3$-$C_8$alkenyl, $C_3$-$C_8$alkynyl, $C_2$-$C_{10}$haloalkyl containing 1 to 6 halogens selected from the group consisting of fluoro, chloro and bromo, $C_2$-$C_{10}$ alkoxyalkyl, cycloalkyl or cycloalkenyl of 3 to 8 ring carbon atoms optionally mono- or di-substituted by fluoro, chloro, bromo or $C_1$-$C_2$alkyl, cycloalkylalkyl or cycloalkenylalkyl of 4 to 10 carbon atoms in which the alkyl portion is of 1 to 3 carbon atoms and the cycloalkyl or cycloalkenyl ring is of 3 to 8 carbon atoms and is optionally mono- or di-ring substituted by fluoro, chloro, bromo or $C_1$-$C_2$alkyl or

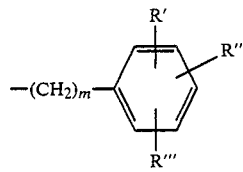

m is 0 to 3,
R' and R'' are independently H, $C_1$-$C_4$alkoxy, $C_1$-$C_4$alkylthio, $CF_3$, fluoro, chloro, bromo or $NO_2$,
R is H, $C_1$-$C_3$alkyl, fluoro, chloro or bromo, or
two of R', R'' and R''' together form $C_1$-$C_2$alkylenedioxy with the other being H,
or a salt form thereof.

2. A compound of claim 1 in which A is —OCH$_2$— and Z is oxygen.
3. A compound of claim 2 in which R is $C_1$-$C_{12}$alkyl.
4. A compound of claim 3 in which R is $C_1$-$C_6$alkyl, in a non-salt form.
5. The compound of claim 4 in which R is methyl.
6. The compound of claim 4 in which R is hexyl.
7. The compound of claim 4 in which R is isopropyl.
8. The compound of claim 4 in which R is n-butyl.
9. The compound of claim 4 in which R is t-butyl.
10. The compound of claim 2 in which R is H, in non-salt form.
11. A compound of claim 2 in which R is a salt-forming cation, in such mono-salt form.
12. A compound of claim 11 in which the salt-forming cation is an alkali metal or ammonium cation.
13. A compound of claim 1 in non-salt form.
14. A compound of claim 2 in which R is

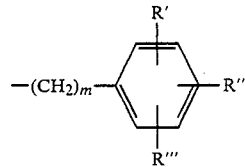

15. A compound of claim 14 in which m is 0 or 1, R' is H, $C_1$-$C_4$alkyl, $C_1$-$C_2$alkoxy, $CF_3$, halo of atomic weight of from 18 to 80 or nitro, R'' is H and R''' is H, $C_1$-$C_2$alkyl, or halo of atomic weight of from 18 to 80.
16. A compound of claim 2 in which Z is oxygen and R is cycloalkyl or cycloalkenyl of 3 to 8 ring carbon atoms optionally mono- or di-substituted by fluoro, chloro, bromo or $C_1$-$C_2$ alkyl.
17. The compound of claim 16 in which R is cyclopentyl, in non-salt form.
18. An agricultural composition comprising an inert agriculturally acceptable carrier and a herbicidally effective amount of a compound of claim 1.
19. A method of combatting weeds in a locus comprising applying to said locus a herbicidally effective amount of a compound of claim 1.
20. The method of claim 18 in which A is —OCH$_2$— and Z is oxygen.
21. The method of claim 19 in which R is $C_1$-$C_6$alkyl.

* * * * *